United States Patent
Pivetau et al.

(10) Patent No.: US 6,632,649 B1
(45) Date of Patent: Oct. 14, 2003

(54) **PROCESS FOR PRODUCING BURKHOLDERIA CEPACIA IN THE PRESENCE OF TERT-BUTANOL OR TERT-A

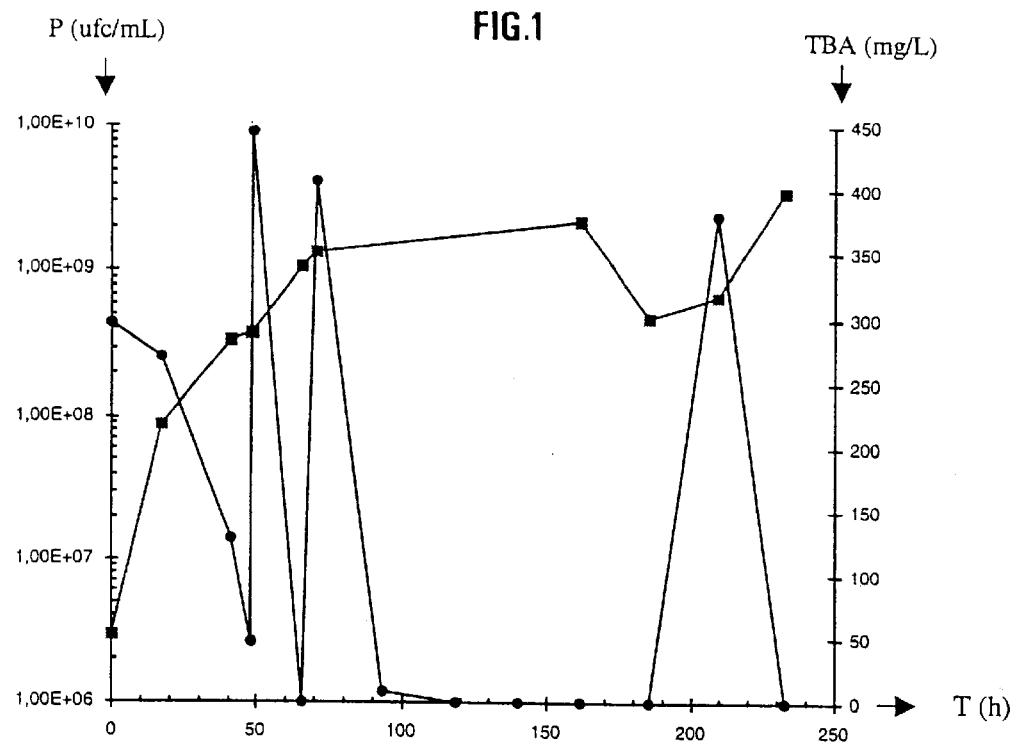
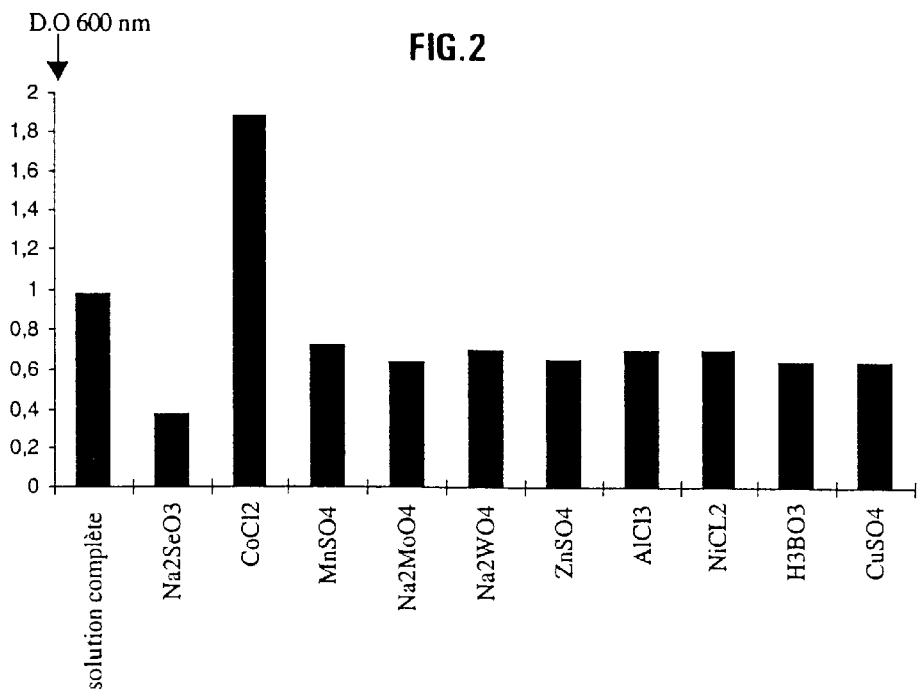

PROCESS FOR PRODUCING BURKHOLDERIA CEPACIA IN THE PRESENCE OF TERT-BUTANOL OR TERT-AMYL ALCOHOL, THE INOCULUM PRODUCED, AND A PROCESS FOR DEGRADING SAID ALCOHOLS

The invention relates to a process for producing microorganisms, *Burkholderia cepacia* (ex *Pseudomonas cepacia*), CIP I-2502, to the inoculum produced, and to its application in a process for degrading the alcohols produced, for example during degradation of ethers known as ether fuels when they are contained in aqueous effluents. The ethers are as follows: ethyl tert-butyl ether, hereinafter termed ETBE, methyl tert-butyl ether, hereinafter termed MTBE, and tert-amyl methyl ether, hereinafter termed TAME. The alcohols produced during their degradation are tert-butanol, hereinafter termed TBA or tert-amyl alcohol, hereinafter termed TAA.

Its particular industrial application is to water treatment.

The prior art is illustrated by the document: "Transformation of carbon tetrachloride by Pseudomonas sp; strain KC under denitrification conditions", Appl. Environ. Microbiol., vol 56, No. 11, Nov, 1990 (1990-11), p. 3240–3246, and by European patent EP-A-0 237 002 and French patents FR-A-2 735 497 and FR-A-2 766 478.

TBA and TAA are degradation products of the ethers MTBE and ETBE and of TAME respectively. Such ethers are currently used or can be used as additives to gasoline for which they increase the octane number. They are widely used since, for example, MTBE is added to gasoline in an amount of 10% to 15% (v/v). For this reason, the presence of such ethers in aquifers is being noted increasingly frequently (Andrews C., 1998, "MTBE—A Long Term Threat to Ground Water quality", Ground Water, 36: 705–706)). Partial biodegradation of such ether fuels in aquifers due, for example, to limited available oxygen, can thus result in an accumulation of TBA and TAA as secondary contaminants.

Further, TBA and TAA can themselves be used as additives to gasoline to increase their octane number and in that case, their use may involve dispersing them in the environment as primary contaminants.

The presence of TBA or TAA in aquifer water for supplying drinking water or in residual water arriving at purification stations necessitates the use of specialised microorganisms which can degrade such alcohols, which latter are relatively resistant to biodegradation because of their branched structure.

According to United States patent U.S. Pat. No. 4,855, 051, bacteria isolated from the earth, *B. coagulans* ATCC 53595, *A. globiformis* ATCC 53596 and *P. stutzeri* ATCC 53602, can degrade TBA added to a minimum mineral medium. According to U.S. Pat. No. 5,811,010, bacterial consortia are also capable of degrading TBA but the microorganisms constituting it have not yet been characterized. Further, in U.S. Pat. No. 5,814,514, different bacteria which are capable of growing on propane are capable of degrading TBA.

The Applicant has isolated an anerobic bacteria, *Burkholderia cepacia* CIP I-2052, for its ability to use TBA as a source of carbon and energy by degrading it to carbon dioxide (mineralisation). This bacteria was deposited by the Applicant as deposit number 1-2052 on Jul. 20, 1998 at the Institut Pasteur collection (CNCM [Collection Nationale de Cultures de Microorganisms, National Collection for Microorganism Cultures], 25 rue du Docteur-Roux, F-75724, Paris). This bacterium, according to the Applicant's French patent application FR-A-2 766 478, can be used in mixed culture with bacteria that are capable of using ETBE as a carbon and energy source by degrading it to the TBA stage which then accumulates in the culture medium; for this reason, addition of an inoculum of *Burkholderia cepacia* CIP I-2052 with the ability of acting on the TBA produced, can produce total degradation of ETBE in effluents. In general, the incubation period for these microorganisms on the substrate is long; for example 400 h are required to degrade about 700 mg/l of TBA, and on the industrial scale, it turns out to be vital that a sufficient quantity of biomass is produced.

The aim of the present invention is to describe a modification to the *Burkholderia cepacia* CIP I-2052 bacteria culture which can very easily improve its growth in the presence of TBA or TAA provided as the only source of carbon and energy by adding a cobalt salt, used alone or as a mixture, to the culture medium.

More precisely, the invention concerns a process for producing a *Burkholderia cepacia* CIP 1-2052 bacterium in which said bacterium is cultured in the presence of air or oxygen and in the presence of a medium containing at least one source of nitrogen, tert-butanol (TBA) and/or tert-amyl alcohol (TAA), and an inoculum is recovered, characterized in that said medium contains at least one cobalt salt. The cobalt is preferably used in its divalent form.

In one embodiment of the process, the cobalt salt can be selected from the group formed by the chloride ion, the sulphate ion, the nitrate ion or a mixture thereof. It has been observed that hexahydrated cobalt chloride has a large effect on the biomass produced by the bacteria.

In a further embodiment of the invention, the bacterium *Burkholderia cepacia* CIP I-2052 can be seeded onto a saline vitamin-containing culture medium to which cobalt chloride has been added, used alone or as a mixture with other oligo-elements, in a final concentration in the medium of 0.01 to 4 mg/l, advantageously 0.03 to 2 mg/l and preferably 0.05 to 0.1 mg/l. Under these conditions, the carbon-containing substrates of *Burkholderia cepacia* CIP I-2052, i.e., TBA or TAA, can be added in to a concentration in the range 0.001 to 10 g/l of medium, preferably in the range 0.2 to 5 g/l.

Under these conditions, an inoculum with a higher cell density than that previously observed is produced wherein the final biomass concentration is, for example, of the order of 0.6 g dry weight/l of culture for an initial TBA concentration of 1 g/l. The inoculum thus prepared can be used alone to treat effluents containing TBA or TAA or it could also be used in a mixed culture with bacteria degrading ETBE or MTBE to TBA or TAME to TAA.

This inoculum produced in large quantities by the process of the invention can also be used directly to purify aqueous effluents containing TBA or TAA or the mixture of TBA and TAA. More precisely, the invention concerns a process for degrading TBA and/or TAA contained in aqueous effluents, in which an inoculum produced by the process for producing a *Burkholderia cepacia* CIP I-2052 bacterium is employed under aerobic conditions.

According to the Applicant's French patent application FR-98/16520, the TBA can originate from degradation of MTBE or ETBE contained in aqueous effluents under aerobic conditions, by at least one bacterium which can be *Gordona terrae* CIP I-1889 or *Rhodococcus equi* CIP-2053. *Gordona terrae* CIP I-1889 was deposited under the terms of the Budapest Treaty by the Applicant as IFP-2001 on Jun. 25, 1997 and *Rhodococcus equi* CIP-2053 was deposited under the terms of the Budapest Treaty by the Applicant as IFP-2005 on Jul. 20, 1998. Both deposits were made at the Institut Pasteur collection (CNCM [Collection Nationale de Cultures Microorganisms, National Collection for Microorganism Cultures], 25 rue du Docteur-Roux, F-75724, Paris). These same bacteria can also degrade TAME or TAA under aerobic conditions.

The invention will be better understood from the accompanying figures illustrating the invention, in which:

FIG. 1 represents the degradation of TBA by *B. cepacia* CIP I-2052 and its growth P (cfu.ml$^{-1}$) in the presence of a solution of oligo-elements, as a function of time;

FIG. 2 shows the effect of certain mineral elements on the production of biomass by *B. cepacia* CIP I-2052.

EXAMPLES 1A AND 1B (COMPARATIVE)

The *B. cepacia* CIP I-2052 strain was seeded onto MM2 saline mineral medium supplemented with glucose (500 mg.l$^{-1}$) as the carbon and energy source. The composition of the MM2 medium was as follows:

KH$_2$PO$_4$ . . . 1.4 g

K$_2$HPO$_4$ . . . 1.7 g

NaNO$_3$ . . . 1.5 g

MgSO$_4$,7H$_2$O . . . 0.5 g

CaCl$_2$,2H$_2$O . . . 0.04 g

FeCl$_3$,6H$_2$O . . . 0.012 g

Vitamin solution . . . 1 ml

H$_2$O . . . qsp 1 litre

The solution of vitamins had the following composition per litre of distilled water:

Biotin . . . 200 mg

Riboflavin . . . 50 mg

Nicotinamic acid . . . 50 mg

Pantothenate . . . 50 mg p-aminobenzoic acid . . . 50 mg

Folic acid . . . 20 mg

Tiamin . . . 15 mg

Cyanocobalamin . . . 1.5 mg

The culture obtained after 24 hours incubation at 30° C. was used to seed flasks containing 200 ml of TBA-supplemented MM2 medium as the carbon and energy source at different concentrations and to which a solution of oligo-elements was added containing hexahydrated cobalt chloride, in an amount of 10 ml.l$^{-1}$ of MM2 medium. By way of comparison, the oligo-element solution was not added to these same flasks.

The solution of oligo-elements had the following composition:

| | |
|---|---|
| nitrilotriacetic acid | 1.5 g |
| Fe(NH$_4$)$_2$(SO$_4$)$_2$, 6H$_2$O | 0.2 g |
| Na$_2$SeO$_3$ | 0.2 g |
| CoCl$_2$, 6H$_2$O | 0.1 g |
| MnSO$_4$, 2H$_2$O | 0.1 g |
| Na$_2$MoO$_4$, 2H$_2$O | 0.1 g |
| ZnSO$_4$, 7H$_2$O | 0.1 g |
| AlCl$_3$, 6H$_2$O | 0.04 g |
| NiCl$_2$, 6H$_2$O | 0.025 g |
| H$_3$BO$_3$ | 0.01 g |
| CuSO$_4$, 5H$_2$O | 0.01 g |

Each flask was seeded from the 3% (v/v) preculture obtained and incubated at 30° C. on an agitated incubator.

Samples were removed from the flasks at regular intervals to assay the residual TBA by gas chromatography; the optical density at 600 nm was also measured and finally, when all of the initial TBA had been consumed, the total organic carbon (TOC) was measured showing the degree of mineralisation of the TBA.

The results obtained with the different cultures are shown in Table 1 showing the effect of adding oligo-elements on the growth of *B. cepacia* CIP I-2052 in the presence of TBA as the carbon source.

TABLE 1

| Ex | Supplement mode | Initial TBA (mg.l$^{-1}$) | Final TBA (mg.l$^{-1}$) | Final TOC (mg.l$^{-1}$) | Time (h) | Initial OD at 600 nm | Final OD at 600 nm |
|---|---|---|---|---|---|---|---|
| 1A | +oligo-elements | 346.5 | 0 | <10 | 72 | 0.116 | 0.54 |
|  | +oligo-elements | 720 | 0 | <10 | 139 | 0.117 | 0.95 |
|  | +oligo-elements | 1000.5 | 0 | <10 | 139 | 0.122 | 1.1 |
| IB | −oligo-elements | 365.5 | 0 | <10 | 150 | 0.1 | 0.156 |
|  | −oligo-elements | 755.1 | 77.5 | ND* | 400 | 0.1 | 0.132 |
|  | −oligo-elements | 986.8 | 156.2 | ND* | 400 | 0.1 | 0.076 |

ND: not determined.

This table shows that adding the solution of oligo-elements containing cobalt produced complete degradation of the TBA supplied up to a concentration of 1000 mg.l$^{-1}$, for example, substantially reducing the incubation period required. Further, the biomass produced was much higher, as shown by the optical density measurements. The preparation of inoculums for the processes for treating effluents containing large quantities of TBA in large quantities, for example up to several g/l, is thus much easier to carry out.

EXAMPLE 2

The growth of the *B. cepacia* CIP I-2052 was produced strain on TBA provided as the only source of carbon was monitored in a 4-1 fermenter.

A 24 hour inoculum of *P. cepacia* CIP I-2052 on 200 ml of MM2 medium containing glucose (1 g.l$^{-1}$) and supplemented with oligo-elements (1% v/v) at 30° C. with agitation.

The culture medium of the fermenter was the MM2 medium described in Example 1 supplemented with the oligo-element solution described in Example 1 in an amount of 1% (v/v). The initial concentration of TBA in the fermenter was 300 mg.l$^{-1}$. After seeding, the OD was 0.05 and counting, carried out by counting the colonies in serial dilutions plated on Luria medium, resulted in the appearance of an initial cell density of 2.9×10$^6$ cfu.ml$^{-1}$.

The operating conditions for this batch fermentation were as follows:

temperature: 30° C.;

aeration: 41. 1$^{-1}$;

pH: 6.8.

TBA degradation was monitored by GC assay on culture supernatants and the evolution of the bacterial population was monitored by counting the colonies plated on Luria medium and by measuring the optical density.

The results are shown in FIG. 1 where successive additions of substrate were made at 50 hours, 70 hours and 210 hours.

After 50 hours of culture, all of the TBA initially provided had been consumed. A first addition of TBA was then made at a concentration of 450 mg.l$^{-1}$ then, after consumption, a second addition of 400 mg.l$^{-1}$ and a third addition of 380 mg.l$^{-1}$ were made.

The final population obtained was $3.5 \times 10^9$ cfu.ml$^{-1}$ for a final OD at 600 nm of 7.0.

This example clearly shows that inoculums can readily be obtained for use in treating contaminated effluents, for example after fixing the bacteria obtained on a support, for example on a mineral support, on which the effluents to be treated are percolated, if a "biofilter" type process as described in the Applicant's French patent application FR-A-2 787 783 is employed.

EXAMPLE 3

The *B. cepacia* CIP I-2052 strain was seeded onto the saline MM2 mineral medium described in Example 1 supplemented with glucose (500 mg.l$^{-1}$) as the source of carbon and energy. This first culture was used to seed 200 ml of MM2 medium without the addition of oligo-elements and supplemented with TBA (750 mg.l$^{-1}$). This pre-culture, without the addition of oligo-elements, allowed the mineral elements in the medium to become exhausted in order not to bring traces of oligo-elements into the final culture, which would produce false readings in the results.

The pre-culture obtained after 96 hours of incubation at 30° C. was used to seed flasks containing 200 ml of MM2 medium supplemented with TBA as the source of carbon and energy at a concentration of 750 mg.l$^{-1}$. To each of these flasks was added one and only one of the elements forming part of the composition of the solution of oligo-elements described in Example 1, in the same final concentration as that employed when the solution itself was used.

Each flask was seeded from the 3% (v/v) pre-culture obtained then incubated at 30° C. in a stirred incubator.

The optical density at 600 nm was measured after 72 hours of incubation for the different flasks.

The results obtained with the different cultures are shown in FIG. 2.

This figure shows that adding the oligo-elements solution had the positive effect noted in Examples 1 and 2. Adding hexahydrated cobalt chloride at a final concentration in the medium of 1 mg.l$^{-1}$ had a large effect on growth since the optical density obtained when adding cobalt chloride alone was about twice that obtained with the oligo-element solution described in Example 1.

EXAMPLE 4

The experiment of Example 3 was carried out, but instead of using TBA as the source of carbon and energy for the *B. cepacia* CIP I-2052 strain, TAA was used in the same proportion as in Example 3. The results obtained are shown in Table 2 and were identical to those already described for the previous Example.

TABLE 2

| Ex | Supplement mode | Initial TBA (mg.l$^{-1}$) | Final TBA (mg.l$^{-1}$) | Time (h) | Initial OD at 600 nm | Final OD at 600 nm |
|---|---|---|---|---|---|---|
| 4A | +oligo-elements | 700 | 0 | 96 | 0.117 | 0.85 |
| 4B | −oligo-elements | 725 | 90 | 400 | 0.1 | 0.132 |

What is claimed is:

1. A process for preparing an inoculum of *Burkholderia cepacia* CIP I-2052 bacteria, in which said bacteria is cultured in a nutrient medium containing at least one source of nitrogen, at least one of tert-butanol(TBA) and tert-amiyl alcohol (TAA), and at least one cobalt salt in the presence of air or oxygen with the provision that the final concentration of the cobalt salt in the medium is 0.01 to 4 mg/l.

2. The process according to claim 1, in which the at least one cobalt salt is a chloride, a sulphate, a nitrate or a combination thereof.

3. The process according to claim 2, wherein said salt is introduced in a final concentration in the medium of 0.05 to 0.1 mg/l.

4. The process according to claim 2, in which the cobalt salt is a hexahydrated cobalt chloride.

5. The process according to claim 1, in which the cobalt salt is a hexahydrated cobalt chloride.

6. The process according to claim 1, in which the concentration of at least one of tert-butanol and tert-amyl alcohol is 0.001 to 10 g/l medium.

7. The process according to claim 1, wherein said *Burkholderia cepacia* CIP I-2052 bacteria are components of a mixed bacterial culture.

8. The process according to claim 7, wherein said mixed culture comprises bacteria that are capable of using ethyl tert-butyl ether (ETBE) as a carbon and energy source.

9. The process according to claim 1, wherein the cobalt in said at least one cobalt salt is divalent.

10. The process according to claim 1, in which the tert-butanol is degraded, said tert butanol being a product from degradation of methyl tert-butyl ether and ethyl tert-butyl ether, under aerobic conditions, by at least one bacterium selected from the group consisting of *Gordona terrae* CIP I-1889 and *Rhodococcus equi* CIP I-2053.

11. The process according to claim 1, wherein tert-amyl alcohol is degraded, said tert-amyl alcohol being a degradation product of tert-amyl methyl ether, under aerobic conditions, by at least one bacterium selected from the group consisting of *Gordona terrae* CIP I-1889 and *Rhodococcus equi* CIP I-2053.

12. The process according to claim 1, in which the cobalt salt is introduced in a final concentration in the medium of 0.03 to 2 mg/l.

13. The process according to claim 1, in which the cobalt salt is introduced in a final concentration in the medium of 0.05 to 0.1 mg/l.

14. The process according to claim 1, in which the concentration of the at least one of tert-butanol and tert-amyl alcohol is 0.2 to 5 g/l.

15. The process according to claim 1, wherein the final biomass of the inoculum is of the order of 0.6 g dry weight/l of culture for an initial TBA concentration of 1 g/l.

16. The process according to claim 8, wherein said ETBE is degraded to TBA.

* * * * *